US011406655B2

United States Patent
Schambye et al.

(10) Patent No.: US 11,406,655 B2
(45) Date of Patent: Aug. 9, 2022

(54) ONCE-DAILY TREATMENT OF PULMONARY FIBROSIS

(71) Applicant: Galecto Biotech AB, Copenhagen (DK)

(72) Inventors: Hans Schambye, Virum (DK); Anders Pedersen, Lyngby (DK); Paul Ford, West Sussex (GB)

(73) Assignee: Galecto Biotech AB, Copenhagen (DK)

( * ) Notice: Subject to any disclaimer, the term of this patent is extended or adjusted under 35 U.S.C. 154(b) by 0 days.

(21) Appl. No.: 15/572,660

(22) PCT Filed: May 12, 2015

(86) PCT No.: PCT/EP2015/060456
§ 371 (c)(1),
(2) Date: Nov. 8, 2017

(87) PCT Pub. No.: WO2016/180483
PCT Pub. Date: Nov. 17, 2016

(65) Prior Publication Data
US 2018/0133240 A1    May 17, 2018

(51) Int. Cl.
| | | |
|---|---|---|
| A61K 31/7056 | (2006.01) | |
| A61K 31/055 | (2006.01) | |
| A61K 31/4192 | (2006.01) | |
| A61P 11/00 | (2006.01) | |
| A61K 9/00 | (2006.01) | |

(52) U.S. Cl.
CPC ........ *A61K 31/7056* (2013.01); *A61K 9/0075* (2013.01); *A61K 31/055* (2013.01); *A61K 31/4192* (2013.01); *A61P 11/00* (2018.01)

(58) Field of Classification Search
CPC .............. A61K 31/7056; A61K 31/055; A61K 31/3192; A61K 9/0075; A61P 11/00
See application file for complete search history.

(56) References Cited

U.S. PATENT DOCUMENTS

| | | | | |
|---|---|---|---|---|
| 2009/0176717 A1* | 7/2009 | Magnani | ................ | A61K 31/70 514/24 |
| 2014/0121179 A1 | 5/2014 | Henderson et al. | | |

FOREIGN PATENT DOCUMENTS

WO    2014067986 A1    5/2014

OTHER PUBLICATIONS

Paranjpe et al., Int. J. Mol. Sci., 2014, 15, p. 5852-5873. (Year: 2014).*
Sham et al., International Journal of Pharmaceutics, 2004, 269, p. 457-467. (Year: 2004).*
Kou et al., Advanced Drug Delivery Reviews, 2012, 64, p. 220-232. (Year: 2012).*
International Search Report dated Aug. 5, 2015 of corresponding International application No. PCT/EP2015/060456; 3 pgs.
Alison C. MacKinnon, et al., "Regulation of Transforming Growth Factor-β1-driven Lung Fibrosis by Galectin-3", Am.J.Resp.Crit. Care.Med, vol. 185, No. 5, Mar. 1, 2012, pp. 537-546.

* cited by examiner

*Primary Examiner* — Jonathan S Lau
(74) *Attorney, Agent, or Firm* — Maier & Maier, PLLC

(57) ABSTRACT

The present invention relates to a compound of formula (I) for use in a method for treatment of pulmonary fibrosis in a human including administering once-a-day to the narrowest parts of the lung tissue of the human an amount of the compound of formula (I) effective to treat said pulmonary fibrosis.

5 Claims, No Drawings

ONCE-DAILY TREATMENT OF PULMONARY FIBROSIS

TECHNICAL FIELD

The present invention relates to a compound of formula (I) for use in a method for treatment of pulmonary fibrosis in a human, such as Idiopathic pulmonary fibrosis. The invention also relates to pharmaceutical compositions comprising the compound of formula (I) for use in a method for treatment of pulmonary fibrosis in a human. Furthermore the present invention relates to a method for treatment of pulmonary fibrosis in a human. Moreover, the present invention relates to a dry powder inhaler device for administration of a compound of formula (I) once-a-day to the narrowest parts of lung tissue of a human.

BACKGROUND ART

Idiopathic pulmonary fibrosis (IPF) represents a massive worldwide health burden. It is a chronic condition of unknown etiology in which repeated acute lung injury causes progressive fibrosis resulting in destruction of lung architecture, deteriorating lung function with consequent respiratory failure and death. Although idiopathic pulmonary fibrosis (IPF) is the archetypal and most common cause of lung fibrosis, numerous respiratory diseases can progress to pulmonary fibrosis, and this usually signifies a worse prognosis. The median time to death from diagnosis is 2.5 years and the incidence and prevalence of IPF continues to rise. It remains one of the few respiratory conditions for which there are no effective therapies, and there are no reliable biomarkers to predict disease progression. The mechanisms resulting in pulmonary fibrosis are unclear but centre around aberrant wound healing as a consequence of repetitive epithelial injury from an as yet unknown cause. IPF is characterized by fibroblastic foci containing fibroblasts/myofibroblasts which show increased activation response to fibrogenic cytokines such as transforming growth factor-β1 (TGF-β1). There is a big unmet need for drugs for treatment of Idiopathic pulmonary fibrosis.

SUMMARY OF THE DISCLOSURE

The compound of formula I is a novel, dry powdered inhaled therapy for the treatment of IPF. Based on results from a first in human study with single ascending doses it was concluded that the compound of formula (I) is both safe and well tolerated in man and favorable PK parameters support once daily dosing for a specific dose range.

In a first aspect the present invention relates to a compound of formula (I)

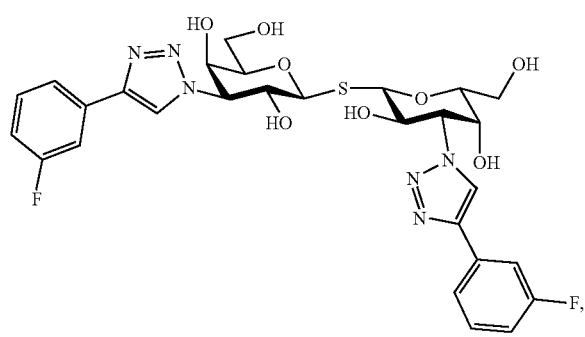

for use in a method for treatment of pulmonary fibrosis in a human comprising administering once-a-day to the narrowest parts of the lung tissue of the human an amount of the compound of formula (I) effective to treat said pulmonary fibrosis.

In a further aspect the present invention relates to a pharmaceutical composition comprising a compound of formula (I)

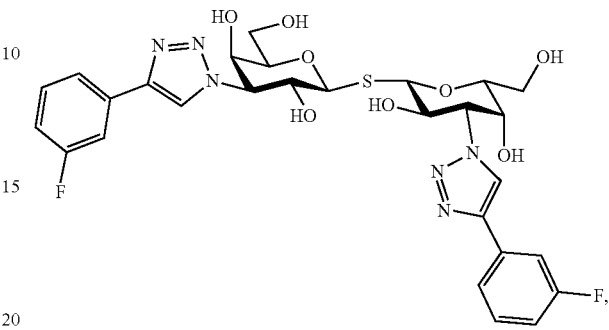

for use in a method for treatment of pulmonary fibrosis in a human comprising administering once-a-day to the narrowest parts of the lung tissue of the human, the composition comprising an amount of the compound of formula (I) effective to treat said pulmonary fibrosis.

In a still further aspect the present invention relates to a method for treatment of pulmonary fibrosis in a human comprising administering once-a-day to the narrowest parts of the lung tissue of the human an amount of a compound of formula (I)

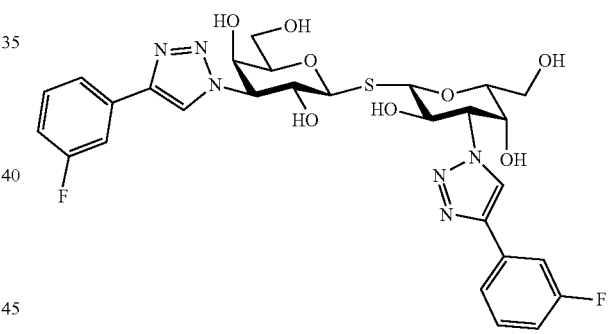

effective to treat said pulmonary fibrosis.

In a further aspect the present invention relates to a dry powder inhaler device comprising a compound of formula (I)

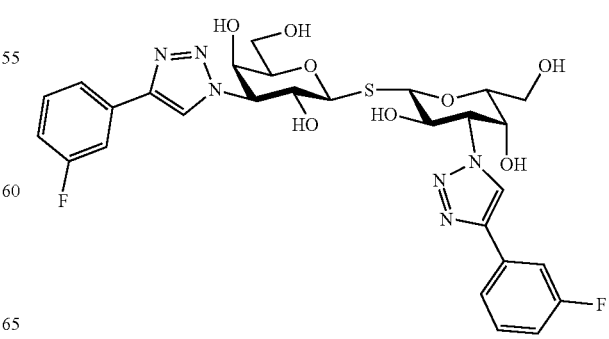

for administration once-a-day to the narrowest parts of lung tissue of a human of an amount of the compound of formula (I) effective to treat pulmonary fibrosis.

DETAILED DESCRIPTION

The compound of formula (I) has the chemical name (IUPAC) bis (3-deoxy-3-(3-fluorophenyl-1H-1,2,3-triazol-1-yl)-β-D-galactopyranosyl)-sulfane, and as used herein is intended to cover the compound of formula (I) in any possible form, such as solid or liquid, a salt, a solvate, or in free form. The compound of formula (I) may be prepared as described in US2014/0121179 or WO2014/067986.

In one embodiment the compound of formula (I) is bis (3-deoxy-3-(3-fluorophenyl-1H-1,2,3-triazol-1-yl)-β-D-galactopyranosyl)-sulfane as the free form.

In a further embodiment the pulmonary fibrosis is Idiopathic pulmonary fibrosis (IPF).

In a further embodiment the administration is carried out by a dry powder inhaler. Typically, a single or multiple dose DPI inhaler is used. In one particular embodiment the dry powder inhaler is RS01 Monodose Dry Powder Inhaler (Plastiape).

When the compound of formula (I) is formulated as a dry powder it may be present in a suitable particle size selected from a mean mass aerodynamic diameter (MMAD) between 0.1 and 20 μm, such as a MMAD between 0.5 and 10 μm, such as between 1 and 5 μm, typically between 2 and 3 μm. In the study described in the Experimental section below the MMAD was measured to 2.5 μm. The selected ranges does not exclude the presence of particles sizes outside these ranges, but the selected ranges are those that provide the desired effect as described herein.

In a still further embodiment the narrowest parts of the lung tissue are the bronchioles and the alveoli.

In a further embodiment the once daily amount is from 0.15 mg to 50 mg, such as 0.15 mg to 1.5 mg, 1.5 mg to 3 mg, 3 mg to 5 mg, 5 mg to 7 mg, 7 mg to 8 mg, 8 mg to 10 mg, 10 mg to 20 mg and 20 mg to 50 mg. In particular the once daily amount form 1.5 mg to 20 mg result in a concentration of the active compound of formula (I) in BAL fluids or macrophages or both of from 1 nM to 100 μM. More preferred concentrations of from 10 nM to 10 μM or more preferred 100 nM to 1 μM can be provided with once daily amount form 3 mg to 10 mg. Based on the results and studies herein it is predicted that a once daily amount of from 1.5 mg to 10 mg, such as 2 mg to 7 mg, will provide local concentrations of the compound of formula I in the lung in a human that will be sufficient to suppress Galectin-3 and provide safe and effective treatment of pulmonary fibrosis.

In a still further embodiment the treatment is chronic treatment.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment is performed in a chronic way. The patient to be treated is a human subject diagnosed with pulmonary fibrosis or other types of lung fibrosis.

The term "an amount effective to treat pulmonary fibrosis" of a compound of formula (I) of the present invention as used herein means an amount sufficient to cure, alleviate or partially arrest the clinical manifestations of pulmonary fibrosis and its complications. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (I) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In one embodiment the pharmaceutical composition contains neat compound of formula I. In some embodiments, the pharmaceutical compositions comprise from 1 to 99 weight % of said at least one pharmaceutically acceptable adjuvant, diluent, excipient and/or carrier and from 1 to 99 weight % of a compound of formula I as herein disclosed. The combined amount of the active ingredient and of the pharmaceutically acceptable adjuvant, diluent, excipient and/or carrier may not constitute more than 100% by weight (100% w/w) of the composition, particularly the pharmaceutical composition. In accordance with the present invention the pharmaceutical composition may consist of neat compound of formula I (that is 100% w/w compound of formula I) or contain a 1-90% w/w, such as 2-20% w/w, for instance a 3% w/w blend of the compound of formula I. Typically, the 3% w/w blend is a pharmaceutical composition containing 3% w/w compound of formula I and 97% w/w lactose carrier. For the clinical trials a 10% w/w blend is used and consist of a pharmaceutical composition containing 10% w/w compound of formula I and 90% w/w lactose carrier.

To the person skilled in the art it is well known that particles with a mean mass aerodynamic diameter (MMAD) between 0.1 and 20 μm (micro meter) have an increased probability of depositing in the terminal bronchial and alveolar regions. This particle size range is ideal for many indications in pulmonary drug delivery, since a portion of the material will still deposit in the upper airways as well. (Cf. Controlled Pulmonary Drug Delivery, Smith and Hickey, Editors, Springer 2011, chapter 13).

In accordance with Controlled Pulmonary Drug Delivery, Smith and Hickey, Editors, Springer 2011 in particular chapters 13, 14 and 15 the skilled person will know how to formulate compounds, such as the compound of formula (I) for pulmonary drug delivery.

Dry powder inhalers (DPI), such as metered dose medicament inhalers are well known for dispensing medicament to the lungs of a patient. Some previous inhalers have comprised a pressurized aerosol dispensing container, wherein the aerosols contain gas propellants in which the powdered medicament is suspended. Upon actuation, the aerosol contents are expelled, through a metering valve, and into the lungs of the patient. Preferred DPIs for use in the present invention is a monodose dry powder inhaler from Plastiape (HQ, Osnago, Italy), in particular the RS01 Monodose Dry Powder Inhaler.

Current designs include pre-metered and device-metered DPIs, both of which can be driven by patient inspiration alone or with power-assistance of some type. Pre-metered DPIs contain previously measured doses or dose fractions in some type of units (e.g., single or multiple presentations in blisters, capsules, or other cavities) that are subsequently inserted into the device during manufacture or by the patient before use. Thereafter, the dose may be inhaled directly from the pre-metered unit or it may be transferred to a chamber before being inhaled by the patient. Device-metered DPIs have an internal reservoir containing sufficient formulation for multiple doses that are metered by the device itself during actuation by the patient. The wide array of DPI designs, many with characteristics unique to the design, will present challenges in developing information in support of an application. Regardless of the DPI design, the most crucial attributes are the reproducibility of the dose and particle size distribution. Maintaining these qualities through the expiration dating period and ensuring the functionality of the device through its lifetime under patient-use conditions will probably present the most formidable challenge.

Pressurized Metered-Dose Inhalers (pMDI) may also be suitable delivery devices for the present compound of formula (I) and are described in Controlled Pulmonary Drug Delivery, Smith and Hickey, Editors, Springer 2011, chapter 8.

Several types of non-aerosol, breath actuated dry powder inhalers have therefore been provided. For example, U.S. Pat. No. 5,503,144 to Bacon, shows a breath-actuated dry-powder inhaler. The device includes a dry powder reservoir for containing a dry powdered medicament, a metering chamber for removal of the powdered medicament from the reservoir in discrete amounts, and an air inlet for entraining the removed powdered medicament through a mouthpiece upon patient inhalation.

U.S. Pat. No. 5,458,135 discloses a method and apparatus for producing an aerosolized dose of a medicament for subsequent inhalation by a patient. The method comprises first dispersing a preselected amount of the medicament in a predetermined volume of gas, usually air. The dispersion may be formed from a liquid or a dry powder. The method relies on flowing substantially the entire aerosolized dose into a chamber that is initially filled with air and open through a mouthpiece to the ambient. After the aerosolized medicament has been transferred to the chamber, the patient will inhale the entire dose in a single breath.

U.S. Pat. No. 6,065,472 discloses a powder inhalation device comprising a housing containing a pharmacologically active compound, a conduit with an outlet extending into the housing through which a user can inhale to create an airflow through the conduit, a dosing unit for delivering a dose of the compound to the conduit and baffles arranged within the said conduit to aid disintegration of powder agglomerates entrained in said airflow.

Regardless of whether an aerosol or non-aerosol inhaler is used, it is of utmost importance that particles of the dispensed dry powder medicament be small enough to ensure the adequate penetration of the medicament into the bronchial region of a patient's lungs during inhalation. However, because the dry powder medicament is composed of very small particles, and often provided in a composition including a carrier such as lactose, non-defined agglomerates or aggregates of the medicament form at random prior to being dispensed. It has therefore been found preferably to provide breath-actuated dry powder inhalers with means for breaking down the agglomerates of medicament or medicament and carrier before inhalation of the medicament.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXPERIMENTAL

The compound of formula I is a novel, inhaled, dry powdered, anti-Galectin 3 small molecule drug therapy being developed for the treatment of IPF. Here we describe results from the First in Human (FIH) study in healthy male volunteers.

Methods

This study was a randomized, double-blind, single center, placebo-controlled, single ascending dose (SAD), phase I study to assess the safety, tolerability, PK (pharmacokinetics) and PD (pharmacodynamics) of the compound of formula I in 36 healthy male volunteers (HV's). 6 dose cohorts of 6 subjects were evaluated using a 4:2 ratio (active: placebo). The compound of formula I was delivered to the lungs of HV's using the RS01 Monodose Dry Powder Inhaler (Plastiape) at the following 6 doses: 0.15 mg, 1.5 mg, 3 mg, 10 mg, 20 mg and 50 mg. The 0.15 mg, 1.5 mg and 3 mg dose was a 3% w/w lactose blend, whereas the 10 mg, 20 mg and 50 mg dose was formulated as neat material. The specific capsule filling weights were 5 mg for the 0.15 mg dose, 50 mg for the 1.5 mg dose, 5 mg for the 10 mg dose and 50 mg for the 50 mg dose. HV's were housed overnight and vital signs, EKG, physical exam, urinalysis and laboratory bloods followed for 14 days. PK blood sampling was taken prior to dosing and then at intervals up to 48 hrs post-dose. Plasma samples for drug concentration measurements were analyzed by the Bioanalytical Unit at Simbec (UK). PK variables were determined using the non-compartmental analysis option in the software WinNONLIN 6.3 from Certara based in Princeton, N.J. 08540 (www.certara.com).

Results

Administration of the compound of formula I was extremely well tolerated at all 6 doses. Adverse events were only mild in nature and included headache, cough and dose-related parageusia (neat blend only) all of which were self-limiting. There were no significant changes from baseline in any of the following parameters; EKG, vital signs, bloods and urinalysis up to 2 weeks post-dose. The compound of formula I was rapidly absorbed, with mean tmax values ranging from 0.8 to 3 hrs, independent of dose. Drug concentrations increased with increasing dose, based on Cmax and AUC and exhibited dose proportionality. t½ is 12 hrs. Clearance (CL/F) is high (~50,000 mL/hr or 900 mL/min) i.e. several fold higher than renal filtration. Given these findings and those consistent with GLP toxicokinetic studies (~90% of the compound of formula I following murine intravenous dosing is found in the feces), it is probable that the liver (via bile excretion) is the major route of elimination in man. Based on radioisotope studies of lung deposition of the compound of formula I in mice, whereby concentrations of the compound of formula I are fifty times greater in the lung than in the circulation, combined with Cmax data from the 3 mg dose at inhaled concentrations used in man, local concentrations of the compound of formula I in the lung in man will be 2 fold in excess of those required to suppress Galectin-3 in lung target cells based on ex-vivo data of suppression of Galectin-3 in human derived macrophages.

CONCLUSION

The compound of formula I is a novel, dry powdered inhaled therapy for the treatment of IPF. Results from this FIH-SAD study indicate that the compound of formula (I) is both safe and well tolerated in man and favorable PK parameters support once daily dosing. Part II of this study is ongoing wherein 24 patients with IPF is continually dosed with ascending doses (0.15 mg, 1.5 mg, 3 mg, 10 mg, 20 mg and 50 mg) of once-daily for 2 weeks with inhaled compound of formula I. Based on these data the compound of formula I could provide a valuable, safe treatment option for patients with IPF in the future.

We claim:

1. A method for treatment of Idiopathic pulmonary fibrosis in a human comprising:
    administering by a dry powder inhaler once-a-day to the narrowest parts of the lung tissue of the human an amount of a compound of formula (I)

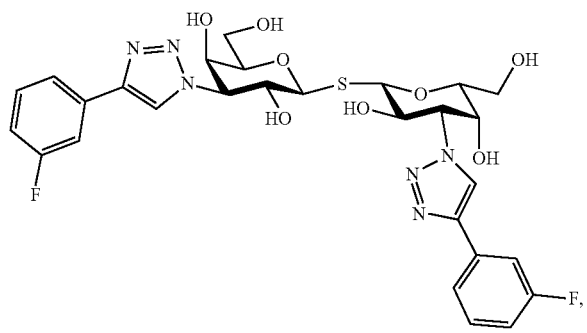

effective to treat said Idiopathic pulmonary fibrosis, wherein the once daily amount is from 1.5 mg to 20 mg of the compound of formula I, wherein the compound of formula I is neat or is a blend with a lactose carrier containing 1 to 20% w/w of compound of formula I, and wherein the compound of formula (I) is formulated as a dry powder present in a suitable particle size selected from a mean mass aerodynamic diameter (MMAD) between 0.1 and 20 μm.

2. The method of claim 1, wherein the compound of formula (I) is bis (3-deoxy-3-(3-fluorophenyl-1H-1,2,3-triazol-1-yl)-β-D-galactopyranosyl)-sulfane as the free form.

3. The method of claim 1, wherein the administration is carried out by a monodose dry powder inhaler.

4. The method of claim 1, wherein the narrowest parts of the lung tissue are the bronchioles and the alveoli.

5. The method of claim 1, wherein the once daily amount is from 3 mg to 20 mg.

* * * * *